United States Patent [19]

Acs et al.

[11] Patent Number: 4,959,323
[45] Date of Patent: Sep. 25, 1990

[54] PRODUCTION AND USE OF PRE S POLYPEPTIDES OF HEPATITIS B VIRUS

[75] Inventors: George Acs, Manhasset, N.Y.; Judith K. Christman, Wyckoff, N.J.; Peter Price, New York, N.Y.; Wolf Offensperger, Bad Duerrheim, Fed. Rep. of Germany; Silke Wahl, Buehl, Fed. Rep. of Germany

[73] Assignee: Mt. Sinai School of Medicine of the City University of New York, New York, N.Y.

[21] Appl. No.: 794,504

[22] Filed: Nov. 4, 1985

[51] Int. Cl.$^5$ .................. C12N 15/63; C12N 15/70
[52] U.S. Cl. .................. 435/320; 435/252.3; 435/252.33; 435/69.1; 435/826; 935/60; 935/65; 935/72
[58] Field of Search .............. 435/68, 80, 91, 235, 435/240, 176.3, 317, 625; 935/12, 29, 38, 156, 65; 536/27; 436/94, 177, 178, 501, 543, 547, 808, 813; 530/324, 325, 326, 350, 820, 821

[56] References Cited

U.S. PATENT DOCUMENTS 4,431,739 2/1984 Riggs .................. 435/253

FOREIGN PATENT DOCUMENTS 0154902 9/1985 European Pat. Off. .

OTHER PUBLICATIONS

Wong et al. (1985) CSH Symp. Abstract (May 2-5 1985 Mtg.).
Offensperger et al. (1985) Proc. Nat'l. Acad. Sci. 82: 7540-7544.
Ono et al. (1983) Nucleic Acids REs. 11: 1747-1757.
Heerman et al. (1984) J. Virology 52: 396-402.
Pardee et al., "The Genetic Control and Cytoplasmic Expression of Inducibility" in the Synthesis of β-Galactosidase by E. Coli, J. Mol. Biol (1959), vol. I., pp. 165-168.
Messing, "A Multipurpose Cloning System Based on the Single-Stranded DNA Bacteriophage M13", Recombinant DNA Technical Bulletin, vol. 2, pp. 43-48, (1979).
Casadaban et al., "In Vitro Gene Fusions that Join an Enzymatically Active β-Galactosidase". . . Translational Initiation Signals, Journal of Bacteriology, Aug. 1980, vol. 143, No. 2, pp. 971-980.
Tiollais et al., "Biology of Hepatitis B Virus", Science, vol. 213, Jul. 24, 1981, pp. 406-411.
Neurath et al., "Enzyme-Linked Fluorescence Immunoassays Using β-Galactosidase. . . Polystyrene Plates", Journal of Virological Methods, vol. 3, (1981), pp. 155-165.
Vieira et al., "The pUC Plasmids, an M13mp7-Derived. . . Synthetic Universal Primers", Elsevier Biomedical Press, Gene. vol. 19 (1982), pp. 259-268.
Christman et al., "Amplification of Expression of Hepatitis B. . . Gene and Cloned Viral DNA", Proc. Natl. Acad. Sci. USA, vol. 79, pp. 1815-1819, Mar. 1982.
Casadaban et al., "β-Galactosidase Gene Fusions for Analyzing Gene Expression in Escherichia coil and Yeast", Methods in Enzymology, vol. 100, 1983, pp. 293-309.
Ullman, "One-Step Purification of Hybrid Proteins which have β-Galactosidase Activity", Elsevier, Gene., vol. 29 (1984), pp. 27-31.
Wain-Hobson et al., "Hepatits B Virus", Genetic Maps 1984, vol. 3, Feb. 1984, pp. 92-98.
Neurath et al., "Location and Chemical Synthesis of a Pre-S Gene Coded Immunodominant Epitope of Hepatitis B Virus", Science, vol. 224, Apr. 27, 1984, pp. 392-395.
Newmark, "In Search of Novel Immunogens", Nature, (News and Views) Oct. 8, 1984, pp. 510-511.
Hermann et al., "Large Surface Proteins of Hepatitis B Virus Containing the Pre-S Sequence", Journal of Virology, vol. 52, No. 2, Nov., 1984, pp. 396-402.
Michel et al., "Synthesis in Animal Cells of Hepatitis B . . . Human Serum Albumin", Proc. Natl. Acad. Sci. USA, vol. 81, Dec. 1984, pp. 7708-7712.
Offensberger et al., "Cloning and Expression of the Pre—S1 Region of the Hapatitis B Virus in E. coli", CSH Molecular Biology of HBV, May 2-5, 1985.
Neurath et al., "Hepatis B Virus Contains Pre-S Gene--Encoded Domains", Nature, vol. 315, May 9, 1985, pp. 154-156.

Primary Examiner—Richard A. Schwartz
Assistant Examiner—S. Nolan

[57] ABSTRACT

In accordance with the present invention, recombinant plasmids are described which, when inserted into microbial hosts, direct the synthesis of proteins in which preS polypeptides found on the surface of human hepatitis B virus are fused to the enzyme β-galactosidase. The recombinant plasmids are produced by inserting DNA sequences encoding the preS polypeptides into the lacZ gene, which codes for E. coli β-galactosidase, carried by the plasmids. Large amounts of the preS-β-galactosidase fusion proteins can be isolated from microbial cultures carrying the recombinant plasmids. Antigenic determinants of fusion protein so produced are recognized by antibodies to the preS determinants of native hepatitis B virus. The β-galactosidase activity of such fusion protein is detected by a suitable chromogenic or fluorogenic substrate. PreS-β-galactosidase fusion proteins so produced can be used in an enzyme-linked immunosorbent assay (ELISA) to diagnose the presence of hepatitis B virus infection. Additionally, the fusion proteins can be cleaved to release preS polypeptides which can be further purified. PreS polypeptides obtained from these fusion proteins can be used to immunize patients against hepatitis B virus.

10 Claims, No Drawings

PRODUCTION AND USE OF PRE S POLYPEPTIDES OF HEPATITIS B VIRUS

BACKGROUND OF THE INVENTION

The present invention relates to a novel composition and novel method for detecting an infection by hepatitis B virus (HBV).

Although many viruses can infect human liver, the major human viral hepatitides are caused primarily by infection with hepatitis viruses (types A, B, non-A, and non-B). These viruses cause acute and chronic liver disease which results in significant morbidity and mortality. Hepatitis B, which has a worldwide distribution is the most prevalent form in adults. In addition to acute and chronic liver disease, chronic hepatitis B virus infection can lead to hepatocellular carcinoma, in areas of the world where infection is endemic.

Since hepatitis B virus is medically important, significant effort has been made to understand the biology of the virus and develop diagnostic tests and prophylactic measures. Hepatitis B virus is a DNA virus. Infectious sera or plasma from individuals with hepatitis contain 22 nm spherical and filament particles that do not contain DNA and represent free virus envelopes. Infectious hepatitis B virus is the 42 nm "Dane" particle, which consists of an envelope and a 27 nm nucleocapsid containing DNA. Free nucleocapsids can be observed in the nucleus of infected hepatocytes but are not found in plasma.

Hepatitis B virus possesses several different major antigens which elicit an immune (antibody) response to the virus and form the basis for long term protective immunity. These include hepatitis B surface antigen (HBsAg), the major envelope antigen, which is found on both the 22 nm and Dane particles. Another surface antigen, termed preS is also found on intact virions and envelopes in serum. Although present in very low abundance, this antigen appears to have significant biologic importance. Recent studies have suggested that hepatitis B vaccines would be more effective if the vaccine formulation also included preS. Since antibodies against HBsAg are protective against hepatitis B infection, this antigen has been intensely studied. Current prophylactic measures are directed toward developing vaccines based on HBsAg.

The genome of hepatitis B virus is a small circular partly double-stranded DNA molecule with a single stranded region of variable length. The long (L) strand is linear and has a fixed length of approximately 3200 nucleotides. The short strand is variable in length from 50 to 75% of L strand. Four open reading frames, termed regions S, P, C, and X, have been identified on the L strand.

The S region which encodes the surface proteins of the virus encompasses nucleotide 2848 to nucleotide 833 in the hepatitis B virus genome. The entire region has the potential for directing the synthesis of a protein 389-400 amino acids in length. HBsAg, the predominant envelope component in both infectious virus and 22 nm particles is a 226 amino acid protein encoded by gene S which begins with the methionine codon at nucleotide 155 and ends at nucleotide 833. Two other methionine codons precede the one at nucleotide 155 in the S region. These methionine codons define the limits of preS2 and preS1 genetic regions that code for preS polypeptides which contain 55 (preS2) and 108-119 (preS1) amino acids. preS1 is located in the hepatitis B virus genome to the 5' side of preS2. Initiation of transcription at any of these methionine codons within the S region can potentially yield three distinct proteins, all having the same 226 carboxyl terminal amino acids but different amino terminal sequences. The amino acid sequence of the preS1 polypeptide is located to the amino terminal side of the preS2 amino acid sequence.

PreS sequences are present on the surface of hepatitis B virus particles in very low amounts (at most they may constitute up to 10% of the surface antigens on the virion or 22 nm particle). Studies have indicated that preS polypeptides are biologically significant. For example, preS2 polypeptide binds aggregated human albumin and appears to be involved in the binding of hepatitis B virus to hepatocytes. Antibodies to preS polypeptides can prevent hepatitis B virus attachment to hepatocytes.

The amino terminal 26 amino acid portion of preS2, termed preS (120-145), has been synthesized. Antibodies to hepatitis B virus bind to either free preS (120-145) or preS (120-145) chemically attached to $\beta$-galactosidase, indicating that the amino terminal portion of preS2 is immunodominant.

Because preS determinants elicit the formation of protective antibodies, it would be highly desirable to produce preS polypeptides in sufficient quantities for use as vaccines and in diagnostic tests for hepatitis B infection. However, production of large quantities of the preS polypeptides by previously disclosed techniques, such as purification from hepatitis B virus envelopes or in vitro peptide synthesis is unfeasible. Although recombinant DNA techniques are being used to produce large amounts of a variety of medically useful proteins, including HBsAg, there are no accounts of such techniques being used to produce preS polypeptides.

SUMMARY OF THE INVENTION

In accordance with the present invention, recombinant plasmids are described which, when inserted into microbial hosts, direct the synthesis of proteins in which preS polypeptides found on the surface of human hepatitis B virus are fused to the enzyme $\beta$-galactosidase. The recombinant plasmids are produced by inserting DNA sequences encoding the preS polypeptides into the lacZ gene, which codes for E. coli $\beta$-galactosidase, carried by the plasmids. Large amounts of the preS-$\beta$-galactosidase fusion proteins can be isolated from microbial cultures carrying the recombinant plasmids. Antigenic determinants of fusion proteins so produced are recognized by antibodies to the preS determinants of native hepatitis B virus. The $\beta$-galactosidase activity of such fusion proteins is detected by a suitable chromogenic or fluorogenic substrate. PreS-$\beta$-galactosidase fusion proteins so produced can be used in an enzyme-linked immunosorbent assay (ELISA) to diagnose the presence of hepatitis B virus infection. Additionally, the fusion proteins can be cleaved to release preS polypeptides which can be further purified. PreS polypeptides obtained from these fusion proteins can be used to immunize patients against hepatitis B virus.

DESCRIPTION OF THE PREFERRED EMBODIMENTS

The present invention provides proteins in which preS polypeptides found in low abundance on the surface of hepatitis B virus are fused to $\beta$-galactosidase.

These fusion proteins are encoded by recombinant plasmids, which have been constructed by inserting genes coding for preS polypeptides into the lacZ gene of plasmids wherein preS genes become fused to the lacZ gene. The plasmids can then be inserted into host organisms, which then will produce the fusion proteins PreS-β-galactosidase fusion proteins, which are readily isolated from cultures of host organisms carrying the plasmids, can be used to detect the presence of preS antibodies in a serum sample, thereby facilitating diagnosis of hepatitis B virus infection. Cleavage of the fusion proteins, followed by further purification of preS polypeptides can provide antigenic material suitable for immunization against hepatitis B virus infection.

Plasmids are extrachromosomal, circular, double-stranded segments of DNA. Because they include at least one replication-initiation site, plasmids are self-replicating. These extrachromosomal elements have proven useful as vectors for the cloning of DNA derived from a variety of sources, including man, animals, viruses, plants and microbes. Many of the plasmids used for cloning such foreign genes carry genes that confer resistance to antibiotics on host organisms that harbor such plasmids. The occurrence of colonies resistant to a particular antibiotic in a culture allows selection of those organisms harboring the plasmids of interest.

Another way of selecting organisms that have taken up a plasmid is to utilize a plasmid that carries a structural gene encoding an enzyme that is easily identifiable. One such gene is the lacZ gene that encodes *E. coli* β-galactosidase. A number of plasmids have been constructed that contain the lacZ gene and suitable regulatory genes. For the purposes of cloning foreign DNA and obtaining quantities of protein therefrom, a further advantage of using the lacZ gene as described by Casadaban et al., *Methods in Enzymology*, Vol. 100, pp. 293-308 (1983) and Casadaban et al., *Journal of Bacteriology*, Vol. 143, pp. 971-980 (1980) and incorporated by reference herein is that the lacZ gene can be conveniently used for making fusion proteins containing β-galactosidase. Genes from any source can be inserted into the lacZ gene in any plasmid carrying such gene, whereby the foreign gene becomes fused to the lacZ gene. Such recombinant plasmids are then inserted into suitable host organisms from which the hybrid fusion proteins can be isolated. Examples of suitable species of host organisms for such recombinant plasmids include prokaryotes such as the bacteria, *Escherichia coli* (*E. coli*), and yeast such as, *Saccharomyces cerevisiae*.

In particular, the present invention provides several different isolates of a bacterium, *E. coli* K-12 strain M182, from the species *E. coli*, each isolate containing a different recombinant plasmid which produces large amounts of a protein in which preS polypeptides are fused to β-galactosidase. The recombinant plasmids are pWS3, which encodes a preS2-β-galactosidase fusion protein, pWS4, which encodes a preS1-preS2-β-galactosidase fusion protein, and pWS5, which encodes a preS1-8-galactosidase fusion protein. These fusion proteins are easily purified in a single step by affinity chromatography directed towards the β-galactosidase portion of the fusion protein. PreS portions of the fusion proteins have biologic and immunologic characteristics indistinguishable from native preS polypeptides of hepatitis B virus. Such immunologic characteristics can form the basis for a diagnostic test for hepatitis B virus infection. Furthermore, following cleavage of the fusion proteins and subsequent isolation of preS polypeptide portions, preS polypeptides can form the basis for protective immunization against hepatitis B virus infection.

*E. coli* K-12 strain M182 carrying pWS3 (ATCC Accession No. 53309) *E. coli* K-12 strain M182 carrying pWS4 (ATCC Accession No. 53310), and *E. coli* K-12 strain M182 carrying pWS5 (ATCC Accession No. 53311) are on deposit with the American Type Culture Collection.

The following examples illustrate the present invention and are not intended to limit the same.

EXAMPLE A.

Construction of pWS1 and analysis of preS2-β-galactosidase fusion protein

A recombinant plasmid, pWS1, was constructed by inserting the DNA which codes for preS2 into the lacZ' gene of plasmid pUC8, an engineered cloning vector described by Viera and Messing, *Gene*, Vol. 19, pp. 259-268 (1982). The plasmid is available for sale by the Bethesda Research Laboratories and was obtained therefrom. Plasmid pUC8, which allows cloning of doubly digested restriction fragments separately with both orientations in respect to the lac promoter, was linearized at its unique Acc I site. Staggered ends of pUC8 thus formed were filled in using the Klenow fragment of *E. coli* DNA polymerase I (Klenow enzyme). The plasmid was recircularized by ligation with T4 ligase and recloned. The resulting plasmid, termed pUC8a, was digested with PstI, which cuts within the open reading frame for the lacZ' gene, and blunt-ended using the 3' to 5' exonuclease of the Klenow enzyme. SphI linkers were added and the plasmid was digested with SphI. The plasmid was again recircularized by ligation with T4 ligase. This construct (pUC8b) restored the correct reading frame for the lacZ' gene and provided an additional ATG sequence in phase with and 39 bases downstream from the ATG sequence that marks the beginning of the lacZ' gene reading frame A 165 base pair NlaIII restriction fragment (bases 3174-157, hepatitis B virus genome numbering), which encompasses the preS2 region, was obtained from plasmid pTHBV-1 and inserted into the SphI site of pUC8b. Plasmid pTHBV-1, which contains tandem copies of the hepatitis B virus genome in a head to tail arrangement, was constructed previously as described by Christman et al.. *Proceedings of the National Academy of Science*, Vol. 79, pp. 1815-1819 (1982). Two plasmids were isolated following insertion of the prS2 region into pUC8b. Plasmid pWS1 contains the preS2 insert in the proper orientation for the production of a functional fusion protein comprised of preS2 and the amino terminal 146 amino acids of β-galactosidase (14% of the enzyme). Plasmid pWS2 contains the insert in reverse orientation.

Plasmid pUC8 directs the synthesis of an amino-terminal fragment of β-galactosidase (enclodied by the lacZ' gene). The host bacterium for pUC8 is *E. coli* K-12 strain JM83 which is described by Messing, *Recombinant DNA Technical Bulletin*, Vol. 2, pp. 43-48 (1979). The bacterium is maintained for sale by the Bethesda Research Laboratories and was obtained therefrom. Strain JM83 carriers a deletion in the lacZ gene (lacZ ΔM15) which was produced by a ∅80 transducing phage integrated into the bacterial chromosome. Strain JM83 (ara, Δlacpro, str A, thi, ∅80d lacZ ΔM15) produces a carboxyl-terminal fragment of β-galactosidase.

These two non-active β-galactosidase gene fragments, one in pUC8 and the other in JM83, complement each other to produce a functional protein with enzyme activity. Colonies of JM83 transformed with either pUC8 or derivatives of this plasmid with a functional lacZ' gene can be readily distinguished from untransformed cells by their ability to form blue rather than white colonies on agar containing the chromogenic β-galactosidase substrate, 5-bromo-4-chloro-3-indolyl-β-D-galactoside (X-gal). JM83 cells transformed with either pWS1 or pWS2 gave rise to blue colonies with approximately the same frequency as those transformed with pUC8.

Lysates of transformed bacteria were prepared from late-log or stationary cultures in order to characterize proteins produced. Bacteria were pelleted by centrifugation and suspended in 1/20 of the culture volume in 0.1 M Tris-HCl, pH 8.0 buffer, containing 0.5 mg/ml lysozyme, 0.1 mM phenylmethyllsulfonylfluoride, and 5 mM EDTA. After three cycles of freeze-thawing, the suspension was centrifuged at 10,000×G for 10 minutes and the resulting supernatant was assayed for β-galactosidase activity using standard methods as described by Pardee, Jacob, and Monod, *The Journal of Molecular Biology*, Vol. 1, pp. 165–178 (1959).

Table I shows that active β-galactosidase was present in lysates of JM83 cultures transformed by either pWS1 or pWS2. This demonstrated that insertion of the DNA coding for preS2 into the lacZ' gene of pUC8 in either orientation permits sufficient complementation of the lacZΔM15 gene product of JM83 cells to allow production of enzymatically active β-galactosidase. Immunologically detectable preS2 determinants were present, however, only when pWS1 was used to transform JM83 cells (Table I). JM83 cells containing pWS2 did not make immunologically detectable preS2 polypeptide. This indicates that for functional preS2 polypeptide to be made, the DNA coding for preS2 must be inserted into pUC8 in correct 5' to 3' orientation.

TABLE I

EXPRESSION OF β-GALACTOSIDASE AND PRES2-β-GALACTOSIDASE FUSION PROTEIN IN *E. COLI*

| Strain | Total β-galactosidase Units/ml lysate* | preS2-β-galactosidase+ FU/μl lysate |
|---|---|---|
| JM83 | >0.3 | 0.03 |
| JM83/pUC8 | 135 | 0.04 |
| JUM83/pWS1 | 92 | 2.8 |
| JM83/pWS2 | 30 | 0.026 |

*Activity in lysate determined directly as described by Pardee, Jacobs, and Monod, The Journal of Molecular Biology, Vol. 1, pp. 165–178 (1959). One Unit of β-galactosidase is defined as the amount capable of hydrolyzing one nmole of o-nitrophenyl-β-D-galactopyranoside per min. at 28°. The protein content of the lysate estimated from A$_{280}$ nm was 5 mg/ml.
+Activity in lysate proteins precipitated with anti-preS (120–145) and Staphylococcus protein A was measured using 4-methyl-umbelliferyl-β-D-galactosidase as substrate as described by Neurath and Strick, Journal of Virological Methods, Vol. 3, pp. 155–165 (1981). FU = arbitrary fluorescence units = 100x(fluorometer digital readout/fluorometer sensitivity range.) FU/ml lysate precipitated with normal rabbit serum and Staphylococcal A protein were pWS1 = 0

Values shown are from a typical experiment. Levels of β-galactosidase and preS2-β-galactosidase activity found in 6–7 different lysates from the same bacterial strains did not vary by more than 15%.

EXAMPLE B.

Immunoassay to detect the presence of preS2-β-galactosidase fusion protein in *E. coli* lysates PreS2-β-galactosidase fusion protein was detected by an immunoassay similar to one used for measuring the reaction between rabbit antibodies to synthetic preS (amino acids 120–145) chemically conjugated to β-galactosidase as described by Neurath, Kent, Strick, Taylor, and Stevens, *Nature*, Vol. 315, pp. 154–156 (1985).

Briefly, 50 μl samples of serial dilutions of bacterial lysates (in 0.01 M Tris-HCl buffer, pH 7.2, containing 0.14 M NaCl, 0.02% NaN3, and 1% bovine serum albumin) were mixed with 450 μl. of rabbit antiserum to synthetic preS (120–145) diluted approximately 200-fold in the same buffer. Other experiments used rabbit antisera to hepatitis B virus from which detectable antibodies to HBsAg had been removed. Following incubation of the mixture for 30 minutes at 37° C., 100 μl of a 10% suspension of *Staphylcoccus aureus* bearing protein A, which is known to bind to the Fc region of IgG immunoglobulins, was added. After a further incubation for 30 minutes at room temperature, the bacteria were pelleted by centrifugation and washed two times with the buffer described above. β-galactosidase activity bound to protein A was determined fluorometrically using 4-methylumbelliferyl-β-D-galactoside as substrate as described by Neurath and Strick, *Journal of Virological Methods*, Vol. 3, pp. 155–165 (1981). Cleavage of this substrate yields the fluorescent compound, 4-methylumbelliferone. All results were corrected for non-specific trapping or adsorption of β-galactosidase in the presence of diluted normal rabbit serum.

EXAMPLE C.

Immunologic characterization of the antigenic determinants of preS2

PreS2-β-galactosidase fusion protein was precipitated from the lysates of JM83 cells transformed with pWS1 by antisera to either synthetic preS(120–145) or hepatitis B virus. The assay used was that described in Example b. Although lysates of JM83 cells transformed by pWS2 contained β-galactosidase activity, no concurrent immunoreactivity of the lysate proteins with antisera to synthetic preS (120–145) or hepatitis B virus was found. This indicated that preS-β-galactosidase fusion protein was not produced by JM83 cells transformated by pWS2. For the fusion protein to contain a functional preS2 polypeptide, as measured by immunologic reactivity, the DNA sequence coding for preS2 must be inserted into pUC8 in the correct 5' to 3' orientation. The results showed that whereas pWS1 contains the DNA sequence coding for preS2 inserted in the correct orientation, pWS2 does not.

The fusion protein produced by JM83 transformed by pWS1 was further characterized using inhibition studies to determine the immunological relationship between the fusion protein and either the synthetic preS (120–145) which comprises the amino terminal 26 amino acids of preS2 or native preS2 protein on hepatitis B virus particles. Briefly, 20 μl of lysate from JM83 cells transformed with pWS1 were mixed with either diluted antiserum to synthetic preS (120–145) or diluted antiserum to hepatitis B virus from which antibodies to HBsAg had been removed. Increasing amounts of either synthetic preS (120–145) or hepatitis B virus particles were used as inhibitors. Inhibition was detected by a decrease in β-galactosidase activity in the immune precipitates as represented by reduced fluorescence in the precipitates. Results were expressed as percent fluorescence inhibition.

Synthetic preS (120-145) and hepatitis B virus particles completely inhibited the reactions between the fusion protein and either antisera. This indicated that the amino terminal 26 amino acid segment of preS2-β-galactosidase fusion protein, synthetic preS (120-145), and native preS2 from hepatitis B virus envelopes was antigenically similar, if not identical. These results also indicate that the amino terminal half of preS2 is the immunologically dominant part of the molecule.

EXAMPLE D.

Quantitation of preS2 peptide in lysates of JM83 transformed by pWS1

The concentration of preS2-β-galactosidase fusion protein in lysates from pWS1 transformed JM83 cells was estimated. It was assumed that antisera bound equivalently to synthetic preS (120-145) and preS2 sequences in the fusion protein. A concentration of synthetic preS (120-145) which produces 50% inhibition of antibody binding by preS2-β-galactosidase fusion protein was determined. A typical concentration was approximately 10 ng per 20 μl of synthetic preS (120-145). Since preS (120-145) has a molecular weight of 2,945 daltons, the calculated concentration of preS2-β-galactosidase fusion protein in the lysate tested was 0.17 μM. A late-log culture of JM83 transformed by pWS1, therefore, contains approximately 40 μg per liter of preS2.

EXAMPLE E.

Construction of pWS3, a high expression vector for production of preS2-β-galactosidase fusion protein The tests set forth in Examples A-D clearly demonstrate the feasibility of producing in E. coli a preS2-β-galactosidase fusion protein with antigenic properties of native preS. Recombinant plasmid pWS3, which would yield large amounts of this fusion protein, was constructed by ligating a 187 base pair BamHI/HindIII fragment of pWS1 DNA containing the preS2 sequence to the lacZ gene of BamHI and HindIII cleaved pSKS105 obtained from M. J. Casadaban and described in Casadaban et al., Methods in Enzymology. Vol. 100, pp. 293-308, (1983). Plasmid pSKS105, which is a high expression vector derived by inserting the lacZ gene into pBR322, is known to lead to highly efficient production of β-galactosidase in E. coli K-12 strain M182 Δ[lac IPOZYA)X74, gal U, gal K, strA$^r$] obtained from M. J. Casadaban and described in Casadaban et al., Journal of Bacteriology, Vol. 1432, pp. 971-980 (1980). Strain M182 by itself will not produce β-galactosidase. Proper 5' to 3' orientation of the preS2 DNA sequence with respect to the lacZ gene of pSKS105 was preserved. M182 cells transformed by pWS3 were detected, as described in Example A, by the ability to form blue colonies on X-gal agar plates.

Lysates of M182 cells transformed by pWS3 were tested for β-galactosidase activity and functional preS2-β-galactosidase fusion protein as described in Examples A-C. A unit of activity was defined as the amount of enzyme capable of hydrolyzing one nanomole of o-nitrophenyl-β-D-galactopyranoside per minute at 28° C. A standard curve relating enzyme activity to incremental known concentrations of purified β-galactosidase was derived. Aliquots of lysate were analyzed under identical conditions and activities obtained were compared to the standard curve. Based on such calculations, a typical late-log or stationary culture of M182 transformed by pWS3 could produce approximately $7 \times 10^6$ activity units or 200 mg f β-galactosidase per liter of culture. Since a fusion protein composed of β-galactosidase (molecular weight of 116,000 daltons) and preS2 (molecular weight of approximately 6000 daltons) is about 5% by weight preS2, the culture produces an estimated 10 mg/1 of preS2 polypeptide.

Alternatively, the amount of preS2 produced could be determined using the 50% inhibition method described in Example c. The value obtained using the inhibition method reasonably agrees with the value derived from using the β-galactosidase standard curve. In either case, the pWS3 transformed M182 cells expression system results in a significant (150-250 fold) increase in preS2 peptide production when compared with the amount produced by JM83 cells transformed by pWS1 given in Example D.

EXAMPLE F.

Purification and analysis of preS2-β-galactosidase fusion protein

PreS2-β-galactosidase fusion protein is a major component of unfractionated lysates from M182 cells transformed by pWS3. The fusion protein can be detected as a stained protein band with an approximate molecular weight of 122,000 daltons when such lysates are analyzed by electrophoresis on polyacrylamide gels containing sodium dodecyl sulfate. This protein band is not present in lysates of untransformed M182 cells or lysates of M182 cells transformed with the parental plasmid, pSKS105. The same protein band (molecular weight of 122,000 daltons) is the only protein detected after electrophoresis of material immunoprecipitated by antibodies to synthetic preS (120-145).

PreS2-β-galactosidase fusion protein can be purified by affinity chromatography on a column of p-aminophenyl-β-D-thiogalactoside-Sepharose ® from lysates of M182 cultures transformed by pWS3. The affinity chromatography column material was prepared and used according to methods for the preparation of such columns and use thereof in isolating fusion proteins containing β-galactosidase described by Ullman, Gene, Vol. 29, pp. 27-31 (1984). The lysate, (diluted in 20mM Tris buffer, pH 7.4, containing 1.6M NaCl, 10mM MgCl2 and 10 mM β-mercaptoethanol, was passed over the affinity column equilibrated in the same buffer. The β-(galactosidase activity which quantitatively bound to the column was eluted with 100mM sodium borate buffer, pH 10.0, containing 10mM β-mercaptoethanol. Table II shows representative purification data. This one-step procedure results in a 75 fold purification of the fusion protein with no loss of enzyme activity. In several tests, recovery of total lysate protein ranged from 85-95% and recovery of preS2-β-galactosidase fusion protein ranged from 95-100%. Recovered purified fusion protein represents 1-3% of the total protein in the lysates of M182 transformed with pWS3.

TABLE II

| | AFFINITY PURIFICATION OF PRES2-β-GALACTOSIDASE | | |
|---|---|---|---|
| Fraction | Protein (mg) | β-galactosidase (Units*) | Specific Activity (U/mg) |
| Load | 517 | 300,000 | 580 |
| Wash | 450 | >0.3 | 0 |
| Borate eluate | 6.9 | 300,000 | 43,000 |

*A Unit of β-galactosidase is defined as the amount capable of hydrolyzing one nmole of o-nitrophenyl-β-D-galactopyranoside per min at 28°.

EXAMPLE G.

Construction of pWS4, a second high expression vector, and purification of a preS1-preS2-β-galactosidase fusion protein A second high expression recombinant plasmid, pWS4, was constructed which, when inserted into strain M182, elicits the production of a second fusion protein, preS1-preS2-β-galactosidase. The restriction enzymes BglII and XhoI were used to obtain a 473 base pair fragment (bases 2839 to 129, hepatitis B virus genome numbering) from pTHBV containing preS1 and preS2 DNA sequences. Plasmid pWS4 was derived by inserting the 473 base pair fragment into pWS3. Plasmid pWS3 was linearized by digestion with XmaI. The staggered ends thus formed were filled in using the Klenow enzyme and the plasmid was religated by T4 ligase. This recircularized pWS3 was digested with BamHI and with XhoI which cut the plasmid DNA at base 129 (hepatitis B virus genome numbering) in the sequence coding for preS2. The digestion removed some preS2 DNA sequence from pWS3 with remaining preS2 sequence having a 5' end at base 129. The 473 base pair fragment which 3' end is base 129 was inserted in proper 5' to 3' orientation into the BamHI/XhoI digested pWS3 resulting in plasmid pWS4 which contains both preS1 and preS2 sequences fused to the lacZ gene. M182 cells transformed by pWS4 were detected, as described in Example A, by the presence of blue colonies on X-gal agar plates.

Lysates of M182 transformed by pWS4 contain high levels of β-galactosidase activity present as a preS1-preS2-β-galactosidase fusion protein with an approximate molecular weight of 134,000 daltons. The fusion protein contains preS2 antigenic determinants reactive with the rabbit antibody to synthetic preS (120–145). Additionally, a hybridoma-derived monoclonal antibody to preS1 polypeptide described by Heermann et al., Journal of Virology, Vol. 52, pp. 396–402 (1984) and obtained from Dr. W. H. Gerlich, Goettingen, W. Germany reacts with preS1 antigenic determinants in this fusion protein.

The preS1-preS2-β-galactosidase fusion protein can be purified to homogeneity in a single step by affinity chromatography as described in Example F. The protein migrates as a single band on SDS polyacrylamide electrophoresis. That preS1 and preS2 determinants are present in the same protein can be demonstrated by sequential precipitation using the preS (120–145) antibody and preS1 monoclonal antibody. All analyses, indicate that pWS1-directs the synthesis of a second fusion protein, preS1 pre S2-β-galactosidase.

EXAMPLE H.

Construction of plasmid pWS5

Plasmid pWS5, a third recombinant high expression vector, is constructed by inserting a 343 base pair fragment encoding preS1 (bases 2839–3192) obtained by BglII, EcoRI, and Bal31 digestion of pTHBV into the lacZ gene of pSKS105 cleaved with BamHI. The methods for constructing pWS5 are similar to those described in Example E for constructing pWS3. Lysates of cultures of M182 transformed with pWS5 contain a preS1-β-galactosidase fusion protein, antigenic determinants of which are recognized by the preS1 monoclonal antibody. This fusion protein can also be purified by affinity chromatography as described in Example F.

EXAMPLE I.

Use of preS-β-galactosidase fusion proteins as diagnostic reagents for hepatitis B virus infection Fusion proteins containing preS antigenic determinants fused to active β-galactosidase form the basis for an enzyme-linked immunosorbent assay (ELISA) for detection of hepatitis B virus antibodies as an aid in diagnosis. Serum from an individual with suspected hepatitis B virus infection is appropriately diluted and added to wells in a 96-well polystyrene microtiter plate. Following a sufficient time to allow antibodies in the serum to bind to the plates, the plates are washed and then further incubated with a different non-specific protein blocking agent (usually diluted gelatin or bovine serum albumin) to prevent any non-specific binding of proteins in subsequent steps. The plates are again washed and an experimentally-defined concentration of preS-β-galactosidase fusion protein is added and allowed to react with any preS antibodies which were present in the serum sample and are now bound to the polystyrene plate. The plates are again washed and a chromogenic or fluorogenic substrate is added, such as o-nitrophenyl-β-D-galactoside, p-nitrophenyl-β-D-galactoside or 4-methylumbelliferyl-β-D-galactoside, which will yield a color reaction or fluorescence when cleaved by β-galactosidase. This positive reaction indicates the presence of antibodies to preS determinants in a patient's serum. Multiple serum samples can be analyzed simultaneously. In clinical laboratories, the processing of such samples is facilitated by an automatic microtiter plate ELISA reader.

EXAMPLE J.

Isolation of preS polypeptides

The recombinant plasmids described herein encoding preS-β-galactosidase fusion proteins are constructed such that a methionine residue is located in the protein at the sequence junction of preS polypeptide and β-galactosidase. The presence of this methionine allows the use of cyanogen bromide (CNBr), which digests proteins specifically at methionine residues, to cleave the fusion protein into its constituent parts. In plasmid constructs containing both preS1 and preS2, there is a naturally occurring methionine codon which defines the beginning of each polypeptide. CNBr cleavage of fusion proteins containing both preS1 and preS2 should yield both polypeptides.

Fusion proteins purified by affinity chromatography as described in Example F can be cleaved with CNBr. The cleaved proteins are then further purified using these affinity chromatography techniques. Whereas the β-galactosidase portion of a fusion protein will be bound by the affinity column, the preS polypeptide portion can be recovered in the wash. Specific antibodies to preS determinants are then utilized to analyze and further purify preS polypeptides. Isolated preS polypeptides so obtained can be used to immunize against hepatitis B virus infection.

We claim:

1. A recombinant plasmid comprising a lacZ gene and a DNA sequence encoding a preS1 polypeptide, a preS2 polypeptide or both of hepatitis B virus envelope protein wherein the polypeptide sequence is inserted within the lacZ gene.

2. A transformed microorganism of the species Escherichia coli containing a recombinant plasmid comprising a lacZ gene and a DNA sequence encoding preS1 polypeptide sequence, a preS2 polypeptide sequence or both is inserted within the lacZ gene, whereby preS1- or preS2-β-galactosidase fusion proteins are produced by the transformed microorganism.

3. The transformed microorganism according to claim 2, wherein the recombinant plasmids contained in the microorganisms are derived from *E. coli* plasmid pSKS105.

4. The transformed microorganism according to claim 2, wherein the microorganism is *E. coli* K-12 strain M182.

5. The transformed microorganism according to claim 3, wherein the plasmid is pWS3.

6. The transformed microorganism according to claim 3, wherein the plasmid is pWS4.

7. The transformed microorganism according to claim 3, wherein the plasmid is pWS5.

8. The transformed *E. coli* K-12 strain M182 containing the recombinant plasmid pWS3 (ATCC Accession No. 53309).

9. The transformed *E. coli* K-12 strain M82 containing the recombinant plasmid pWS4 (ATCC Accession No. 53310).

10. The transformed *E. coli* K-12 strain M182 containing the recombinant plasmid pWS5 (ATCC Accession No. 53311).

*E. coli* K-12 strain M182 carrying pWS3 (ATCC Accession No. 53309), *E. coli* K-12 strain M182 carrying pWS4 (ATCC Accession No. 53310), and *E. coli* K-12 strain M182 carrying pWS5 (ATCC Accession No. 53311) are on deposit with the American Type Culture Collection

* * * * *

UNITED STATES PATENT AND TRADEMARK OFFICE
CERTIFICATE OF CORRECTION

PATENT NO. : 4,959,323

DATED : September 25, 1990

INVENTOR(S) : George Acs et al.

It is certified that error appears in the above-identified patent and that said Letters Patent is hereby corrected as shown below:

Title page, 1st col., 21st and 20th lines-from-bottom, "Inducibility" in the Synthesis of ß-Galactosidase by E. Coli," should read --Inducibility in the Synthesis of ß- galactosidase by E. Coli",--;

First page, 2nd col., 25th line, "Hapatitis" should read --Hepatitis--;

Col. 1, line 68, "preS1" should read --PreS1--;

Col. 3, line 48, "prokarylotes: should read --prokaryotes-;

Col. 3, line 49, "as," should read --as--;

Col. 3, line 59, "preS1-8-galactosidase" should read --preS1-ß-galactosidase--;

Col. 4, line 40, "frame A" should read --frame. A--;

Col. 4, line 50, "prS2" should read --preS2--;

Col. 4, line 58, "encloded" should read --encoded--;

Col. 4, line 64, "carriers" should read --carries--;

Col. 5, line 48, "JUM83/pWS1" should read --JM83/pWS1--;

Col. 5, line 57, "0" should read --0.033, pWS2=0.020--;

Col. 8, line 1, "f" should read --of--;

Col. 8, line 47, "ß-(galactosidase" should read --ß-galactosidase--;

Col. 8, TABLE II, insert new paragraph after "at 28°." --Data shown are from a representative test in which a lysate containing 300,000 U of ß-galactosidase was diluted in buffer containing 1.6M NaCl, 20 mM Tris, pH 7.4, 10 mM=$MgCl_2$ and 10 mM ß-mercaptoethanol was passed over a 6 ml column packed with p-amino-phenyl-ß-D-thiogalactoside-Sepharose® equilibrated with the same buffer. The column was washed with this buffer until no more protein was eluted and then the fusion protein was eluted

UNITED STATES PATENT AND TRADEMARK OFFICE
CERTIFICATE OF CORRECTION

PATENT NO. : 4,959,323

DATED : September 25, 1990

INVENTOR(S) : George Acs et al.

It is certified that error appears in the above-identified patent and that said Letters Patent is hereby corrected as shown below:

with 100 mM sodium borate, pH 10, 10 mM ß-mercaptoethanol as described by Ullman, <u>Gene</u>, <u>Vol</u>. 29, pp. 27-31 (1984). The values for total enzyme activity and protein content were calculated from assays of ß-galactosidase activity in aliquots of the fractions and from their absorbance at 280nm. In four separate experiments, recovery of total protein ranged from 85-95% and recovery of preS2-gal from 95-100%. Recovered purified preS2-gal comprised 1-3% of the total protein in the lysates.--;

<u>Col. 9, line 52</u>, "pWS1-directs" should read --pWS4 directs--;

<u>Col. 9, line 53</u>, "preS1 pre S2-ß-galactosidase" should read --preS1-preS2-ß-galactosidase--;

<u>Col. 12</u>, delete lines 12-17.

Signed and Sealed this

Sixteenth Day of June, 1992

Attest:

DOUGLAS B. COMER

Attesting Officer

Acting Commissioner of Patents and Trademarks